(12) United States Patent
Guest

(10) Patent No.: US 12,173,271 B2
(45) Date of Patent: *Dec. 24, 2024

(54) ASEPTIC TISSUE PROCESSING METHOD, KIT AND DEVICE

(71) Applicant: INSTIL BIO (UK) LIMITED, Manchester (GB)

(72) Inventor: Ryan Dominic Guest, Manchester (GB)

(73) Assignee: INSTIL BIO (UK) LIMITED, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,103

(22) Filed: Apr. 3, 2023

(65) Prior Publication Data

US 2023/0235269 A1 Jul. 27, 2023

Related U.S. Application Data

(63) Continuation of application No. 17/826,053, filed on May 26, 2022, now Pat. No. 11,618,877, which is a (Continued)

(30) Foreign Application Priority Data

Jan. 13, 2017 (GB) ...................................... 1700621

(51) Int. Cl.
*C12M 3/00* (2006.01)
*C12M 1/00* (2006.01)
(Continued)

(52) U.S. Cl.
CPC ............ *C12M 47/04* (2013.01); *C12M 41/48* (2013.01); *C12M 45/02* (2013.01); *C12M 45/09* (2013.01); *C12M 45/22* (2013.01)

(58) Field of Classification Search
CPC .............................. C12M 45/22; C12M 47/04
See application file for complete search history.

(56) References Cited

U.S. PATENT DOCUMENTS

| | | | | |
|---|---|---|---|---|
| 2002/0168759 | A1* | 11/2002 | Wang | ......................... A61J 1/10 |
| | | | | 435/304.2 |
| 2009/0258417 | A1* | 10/2009 | Tanaka | ................... C12M 23/04 |
| | | | | 435/325 |
| 2018/0250338 | A1* | 9/2018 | He | ....................... A61K 33/243 |

FOREIGN PATENT DOCUMENTS

WO WO-9923199 A1 * 5/1999

* cited by examiner

*Primary Examiner* — Nathan A Bowers
(74) *Attorney, Agent, or Firm* — Alston & Bird LLP

(57) ABSTRACT

This present invention concerns a single use aseptic kit comprising: a disaggregation module for receipt and processing of material comprising solid mammalian tissue; and a stabilization module for storing disaggregated product material, wherein each of said modules comprises one or more flexible containers connected by one or more conduits adapted to enable flow of the tissue material there between; and wherein each of said modules comprises one or more ports to permit aseptic input of media and/or reagents into the one or more flexible containers. The invention further relates to an automated device for semi-automated aseptic disaggregation and/or enrichment and/or stabilisation of cells or cell aggregates from mammalian solid tissue comprising a programmable processor and the single use aseptic kit. The invention further relates to a semi-automatic aseptic tissue processing method.

8 Claims, 11 Drawing Sheets

Related U.S. Application Data continuation of application No. 16/477,366, filed as application No. PCT/GB2018/050088 on Jan. 12, 2018, now abandoned.

(51) Int. Cl.
*C12M 1/33* (2006.01)
*C12M 1/36* (2006.01)

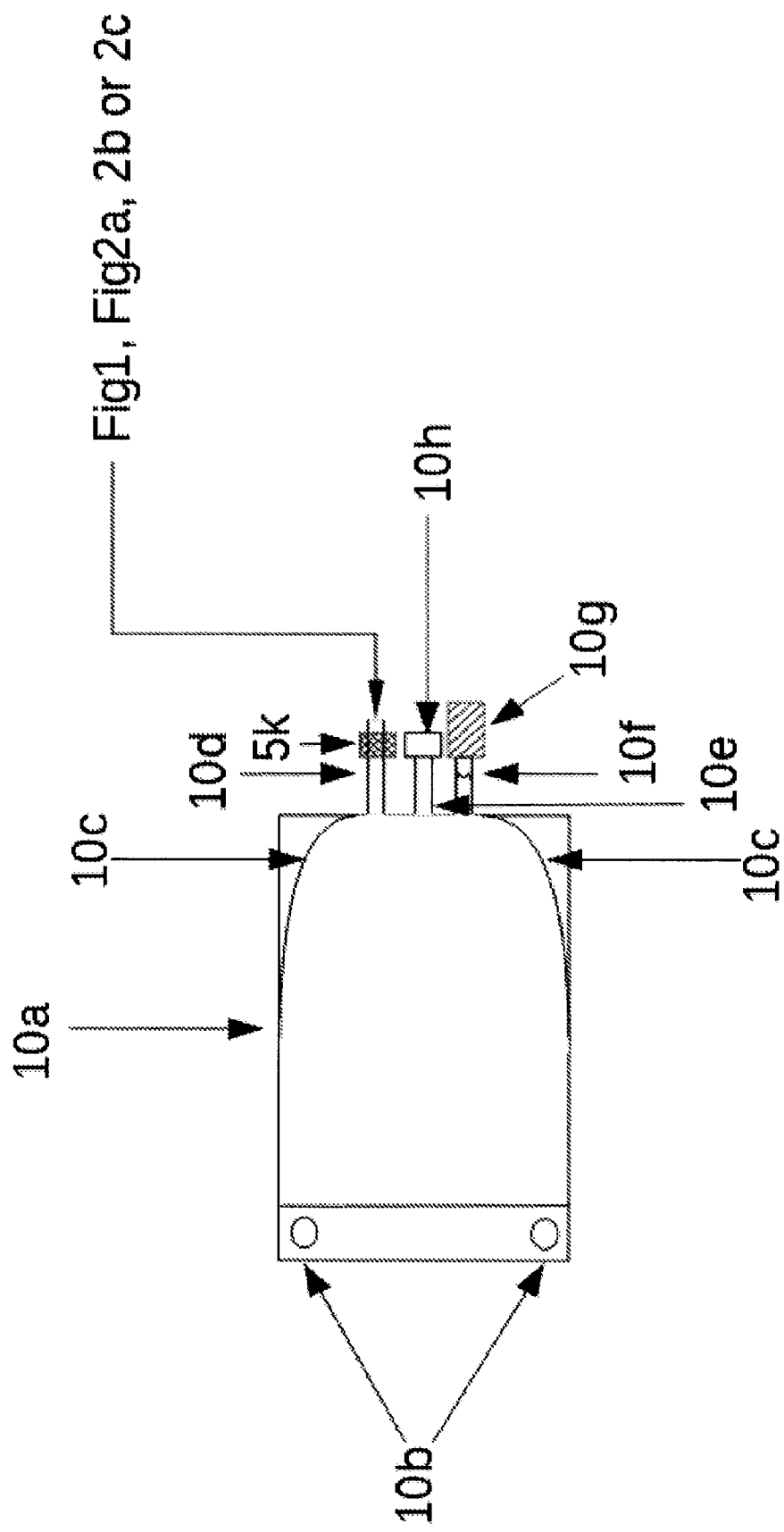

| Tissue Sample Dimensions | Volume of digestion media (ml) | 1st Step | 2nd Step | 3rd Step | Fully disaggregation |
|---|---|---|---|---|---|
| 1 x 1 x 1 (~1 g) | 25 | 3 min disaggregation & 30 min @ 37°C | 1 min disaggregation & 30 min @ 37°C | 1 min disaggregation | Y |
| 1 x 1 x 1 (~1g) | 25 | 1 min disaggregation & 30 min @ 37°C | 1 min disaggregation & 30 min @ 37°C | 1 min disaggregation | Y |
| 1.5 x 1.5 x 1.5 (~3 g) | 25 | 5 min disaggregation & 30 min @ 37°C | 1 min disaggregation & 30 min @ 37°C | 1 min disaggregation | Y |
| 2 x 2 x 2 (~7 g) | 25 | 7 min disaggregation & 30 min @ 37°C | 1 min disaggregation & 30 min @ 37°C | 1 min disaggregation | Y |
| 2 x 2 x 2 (~7 g) | 50 | 10 min disaggregation & 30 min @ 37°C | 1 min disaggregation & 30 min @ 37°C | 1 min disaggregation | N (30-50% intact) |

FIG. 5B

ASEPTIC TISSUE PROCESSING METHOD, KIT AND DEVICE

CROSS-REFERENCE TO RELATED APPLICATIONS

This application is a continuation of U.S. patent application Ser. No. 17/826,053 filed May 26, 2022, which is a continuation of U.S. patent application Ser. No. 16/477,366 filed Jul. 11, 2019, which is a national stage entry of PCT/GB2018/050088 filed Jan. 12, 2018, which claims priority to GB Application No. 1700621.4 filed Jan. 13, 2017, which are hereby incorporated by reference.

The present invention concerns a kit and a semi-automatic device using that kit for aseptic disaggregation of solid tissue derived eukaryotic cells into either single cells or small cell number aggregates. The invention further relates to a semi-automatic aseptic tissue processing method comprising: a process for aseptic disaggregation of solid tissue derived eukaryotic cells into either single cells or small cell number aggregates and their further processing.

BACKGROUND

The conditions during solid tissue disaggregation and time taken to harvest the cells have a substantial impact on the viability and recovery of the final cellularised material. Typically a solid tissue derived cell suspension, that is obtained, comprises a wide variety of different cell types and the disaggregation media and tissue debris or fluids. Often, selective targeting and or isolation of an individual or multiple cell types is prerequisite for the starting material prior to manufacture of regenerative medicines, adoptive cell therapies, ATMPs, diagnostic in vitro studies or scientific research. Generally these selection or enrichment techniques rely on one of the following properties: size, shape, density, adherence or strong protein: protein interactions (i.e. antibody: antigen) or providing a growth supporting environment by controlling the culture conditions or more complex cell marker interactions associated with semi-permanent or permanent coupling to magnetic or non-magnetic solid or semi-solid phase substrates can be used.

For enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells. An especially potent sorting technology is magnetic cell sorting. Methods to separate cells magnetically are commercially available e.g. from Thermo fisher, Miltenyi Biotech, Stem cell Technologies, Cellpro, Seattle, Advanced Magnetics, Boston or Quad Technologies Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching, sorting and/or detecting neuronal cells from a sample containing neuronal cells according the present invention monoclonal antibodies are used in conjunction with colloidal superparamagnetic microparticles having an organic coating by e.g. polysaccharides (Magnetic-activated cell sorting (MACS) technology (Miltenyi Biotec, Bergisch Gladbach, Germany)). These particles (nanobeads or Micro-Beads) can be either directly conjugated to monoclonal antibodies or used in combination with anti-immunoglobulin, avidin or antihapten-specific MicroBeads or coated with other mammalian molecules with selective binding properties.

Magnetic particle selection technologies such as those described above, allows cells to be positively or negatively separated by incubating them with magnetic nanoparticles coated with antibodies or other moieties directed against a particular surface marker. This causes the cells expressing this marker to attach to the magnetic nanoparticles. Afterwards the cell solution is placed within a solid or flexible container in a strong magnetic field. In this step, the cells attach to the nanoparticles (expressing the marker) and stay on the column, while other cells (not expressing the marker) flow through. With this method, the cells can be separated positively or negatively with respect to the particular marker(s).

In case of a positive selection the cells expressing the marker(s) of interest, which attached to the magnetic column, are washed out to a separate vessel, after removing the column from the magnetic field.

In case of a negative selection the antibody or selective moiety used is directed against surface markers(s) which are known to be present on cells that are not of interest. After application of the cells/magnetic nanoparticles solution onto the column the cells expressing these antigens bind to the column and the fraction that goes through is collected, as it contains the cells of interest. As these cells are non-labelled by the selective antibodies or moiety(s) coupled to nanoparticels, they are "untouched".

The known manual or semi-automated solid tissue processing steps are labour-intensive and require a knowledge of the art.

In addition where the material is used for therapeutic purposes, the processing requires strict regulated environmental conditions during handling the cell cultures, for example tissue processing as apart of or prior to disaggregation; enzymatic digestion and transfer into storing devices or incubation conditions for disaggregation/cellularisation and viable tissue yields. Typically this process would require multiple pieces of laboratory and tissue processing equipment, and personal with the skills and knowledge of the scientific art with critical stages contained within either hazard containment or tissue processing facility(s) aseptic environment(s) in order to perform the same activity safely and also minimise the risk of contamination(s).

The invention therefore arises from a need to provide improved solid tissue processing, including an apparatus/device that undertakes said processing that achieves the unmet need described above.

SUMMARY OF INVENTION

The present invention concerns a single use aseptic kit comprising a disaggregation module for receipt and processing of material comprising solid mammalian tissue; an optional enrichment module for filtration of disaggregated solid tissue material and segregation of non-disaggregated tissue and filtrate; and a stabilisation module for optionally further processing and/or storing disaggregated product material, wherein each of said modules comprises one or more flexible containers connected by one or more conduits adapted to enable flow of the tissue material there between; and wherein each of said modules comprises one or more ports to permit aseptic input of media and/or reagents into the one or more flexible containers.

In prior art the tissue may undergo physical and or enzymatic disaggregation/cellularisation in a single container. In the present invention sets of containers which are interconnected and have specific separate functions maintain an aseptically closed system to process, optionally enrich but stabilise the disaggregated and cellularised solid tissue product. Essentially the invention provides a rapid pre-sterilised environment to minimise the time required and risk of contamination or operator exposure during the processing of the solid tissue.

The kit described here allows for closed solid tissue processing eliminating the risk of contamination of the final cellularised product compared to standard non-closed tissue processing. This is especially when the process is performed within a tissue retrieval/procurement site and requires storage prior to final cell processing for its ultimate utility. In addition, safety of the operator is increased due to reduction of direct contact with biological hazardous material which may contain infectious organisms such as viruses.

The kit also enables either all of or a portion of the finally processed cellularised material to be stabilised for either transport or storage prior to being processed for its ultimate utility.

The invention will enable the solid tissue to be processed at the time of tissue retrieval, or later if required, without impact upon the retrieval procedure or the viability of the cellularised product.

In some embodiments employing optional enrichment via a form of physical purification to reduce impurities such as no longer required reagents; cell debris; non-disaggregated tissue and fats. A single cell or small cell number aggregates can be enriched for stabilisation after disaggregation by excluding particles and fluids of less than 5um or incompletely disaggregated material of or around 200 µm across or larger but this will vary upon the tissue and the efficiency of disaggregation and various embodiments in the form of tissue specific kits may be employed depending upon the tissue or ultimate utility of the disaggregated solid tissue.

In some embodiments the one or more flexible containers comprise a resilient deformable material. The one or more flexible containers of the disaggregation module may comprise one or more sealable openings. The one or more flexible containers of the disaggregation module and/or the stabilisation module may also comprise a heat sealable weld.

In further embodiments the one or more flexible containers that are part of any module comprise internally rounded edges.

The one or more flexible containers of the disaggregation module may comprise disaggregation surfaces adapted to mechanically crush and shear the solid tissue therein.

Further, the one or more flexible containers of the enrichment module may comprise a filter adapted to retain a retentate of cellularised disaggregated solid tissue.

In embodiments, one or more flexible containers of the stabilisation module comprise media formulation for storage of viable cells in solution or in a cryopreserved state. In some embodiments the In further embodiments the kit further comprises a radio frequency or other digitally recognisable identification tag so that it may be scanned and recognised during automated processing, such as with/in the automated device in embodiments of the present invention. Crucially the tag provides information about the conditions and steps required to be auto processed, so simply by scanning the kit, any automated system used with the kit to process the tissue can be undertaken without further intervention or contamination. Once the tissue sample has been placed in the disaggregation module, it can for example be sealed, manually, or automatically, before processing begins.

In this regard, in preferred embodiments that include a device, the kit associated tag is detected by the device's processor and the device then runs a specific program according to a type of disaggregation and/or enrichment and/or stabilisation process; one or more types of media used in those processes; including an optional freezing solution suitable for controlled rate freezing. Put another way, the kit is therefore be readable by an automated device used to execute a specific fully automatic method for processing the specific tissue when inserted to such a device.

The invention is particularly useful in a sample processing, particularly automated processing. Thus, in a further aspect the invention concerns use of the single use aseptic kit described above in a semi-automated process for the aseptic disaggregation and/or enrichment and stabilisation of mammalian cells or cell aggregates.

A particular advantage is that solid tissue disaggregation (and optional processes including all described manipulations herein described required to achieve optimal results) can be performed in a closed system, i.e. an aseptic process with minimal risk of contaminations and with minimal user knowledge.

The invention further relates to an automated device for semi-automated aseptic disaggregation and/or enrichment and stabilisation of cells or cell aggregates from mammalian solid tissue comprising a programmable processor and the single use aseptic kit as described in any of the before mentioned examples above.

In embodiments, as previously described, the device may have a comprising radio frequency identification tag reader to recognise the single use kit. The programmable processor is capable of recognising the single use aseptic kit via its tag and subsequently able to execute the kit programme which defines the type of disaggregation, enrichment and stabilisation processes together with the respective media types required for those processes.

In this regard, the programmable processor is adapted to communicate with and control one or more of: the disaggregation module; the enrichment module; and the stabilisation module of the device. The device, including its processor, may therefore have multiple functionality to assess the flow of materials through the kit making decisions of when a step is completed as part of the pre-programmed functions and the feedback the device gets from its sensors.

For example, the programmable processor may control the disaggregation module to enable a physical and/or biological breakdown of the solid tissue material in that container. The programmable processor may also control the disaggregation module to enable a physical and enzymatic breakdown of the solid tissue material.

In some embodiments the enzymatic breakdown of the solid tissue material is by the selection and provision of one or more media enzyme solutions selected from collagenase, trypsin, lipase, hyaluronidase, deoxyribonuclease, Liberase H1, pepsin, or mixtures thereof.

In addition or alternatively the programmable processor may control disaggregation enabling the surfaces within the disaggregation flexible containers to mechanically crush and shear the solid tissue. In embodiments, the disaggregation surfaces are controlled by mechanical pistons, for example.

In some embodiments, the programmable processor controls the stabilisation module to cryopreserve the enriched disaggregated solid tissue in the container, for example, this may be achieved by using a programmable temperature setting, a condition which is determined by reading the tag of the kit inserted in the device.

In some embodiments, to undertake different functions of the process, one or more of the additional components of the device and/or kit are provided. Such features may be available in any combination. This may include for example: sensors in the device capable of recognising whether a disaggregation process has been completed in the disaggregation module of the kit prior to transfer of the disaggregated solid tissue to the optional enrichment module; weight sensors to determine an amount of media required in the containers of one or more of the disaggregation module; the enrichment module; and/or the stabilisation module and means to control that transfer of material between respective containers; and temperature sensors to control the temperature within the containers of the one or more of the disaggregation module; the enrichment module; and/or the stabilisation module.

Other possible features include an optional bubble sensor to control the transfer of media between the input and output ports of each container in the module; one or more pumps may provide means to control the transfer of media between the input and output ports; and/or pressure sensors to assess the pressure within the enrichment module; valves to control an optional tangential flow filtration process within the enrichment module; and/or one or more clamps to control the transfer of media between the input and output ports of each module.

For example, the programmable processor is adapted to maintain an optimal storage temperature range in the stabilisation module until the container is removed; or executes a controlled rate of freezing.

These embodiments of the device and kit allow solid tissue derived cells or cell aggregates to be: stored for short periods (minutes to days) or stored for long periods (multiple days to years) prior to their ultimate utility depending on the type or stabilisation process used with the stabilisation module.

For ease of use, the device of the invention may further comprise a user interface. That interface may comprise a display screen to display instructions that guide a user to input parameters, confirm pre-programmed steps, warn of errors, or combinations thereof.

In many cases it is desirable that the automated device is adapted to be transportable and thus may comprise dimensions that permit easy manoeuvrability and/or aid movement such as wheels, tyres, handles and the like.

The final cellular material product can then be used for but not limited to either: regenerative medicine, adoptive cell therapies, ATMPs, diagnostics or to further the basic scientific understanding of tissue, cell function or organism function.

The combination of an aseptic kit, automated processing device and associated media formulations, which can disaggregate solid tissues to provide functional living cells or the product of the cells for subsequent therapeutic, diagnostic or scientific use, is therefore highly desirable.

In some embodiments the cells produced using the kit and/or device of the invention are useful for providing functional living cells and maybe cultured further for that use. Cell culture is a process by which cells are grown outside the original host using controlled environmental and supportive conditions which vary by cell type and organism. These are often sterile artificial vessels which allow gas and temperature to be maintained and either manual or automated changes in essential nutrients, metabolites, growth factors and gases which enable regulation of the cells requirements to survive and in most cases thrive. Cell culture requirements differ broadly by the type of cell(s) and its required purpose. Cell culture conditions can be optimised for cell expansion, cell differentiation or manufacturing of different phenotypes of the cell or its products. The most commonly varied factor in culture systems is the cell culture medium, for which a vast number of recipes is known (see for example "Cell Culture Techniques" Humana Press, 1st. Edition, 2011)

In some embodiments disaggregated or cellularised material produced by the device and kit can be useful as the starting material to isolate specific cell populations which are grown out using stimulation or non-required cells are inhibited or apoptosis/cell death is induced resulting in a semi/purified population.

Such cells can be further sorted by one or more of the following processes: Fluorescence-activated cell sorting using antibody/protein labelling or natural fluorescence; Magnetic separation of cells, e.g. the magnetic activated cell sorting (MACS technology, Miltenyi Biotec GmbH, Germany). This technology requires a marker that allows direct separation of the cells of interest by an antibody coupled to a magnetic microbead (Miltenyi et al., Cytometry 1990; 11:231-238). Alternatively, where it is not possible or not desirable to actively select the target population a process of negative isolation can be employed. In this approach, non-target cells are magnetically labelled and depleted, thereby leaving the unlabelled cells of interest; Label free cell separation and sorting using physical separation methods where either the target is not known, is a mixed population and physical cell (or clumps of cells) characteristics can be used to separate the cellular material from the current media to: remove impurities or reagents that are no longer required such as enzymes, cell debris, connective tissue, fat & mineral deposits; or exchange fluids which may be better for stabilising the cells for distribution and/or storage. It is envisaged that embodiments of the invention may include such functionality within the parameters of the processor or the automated device and operating system.

For example, the purity, of the disaggregated and cellularised solid tissue product, can be further increased if one or more cell surface marker(s) are used to select for or deplete a subpopulation of cells either as an independent step within the process or after processing using the methods described.

The present invention also relates to a method for enhanced semi-automated disaggregation cellularisation and storage of tissue derived cells. Optionally, steps of enrichment, formulation and cryopreservation are also provided.

In a further aspect of the invention, there is provided a semi-automatic aseptic tissue processing method comprising: automatically determining aseptic disaggregation tissue processing steps and one or more further tissue processing steps and their associated conditions from a digital tag identifier on an aseptic processing kit, optionally in accordance with the kit described herein; placing a tissue sample into a flexible plastic container of the aseptic processing kit; and processing the tissue sample by automatically executing the one or more tissue processing steps by communicating with and controlling the disaggregation module; the optional enrichment module; and the stabilisation module.

The one or more automatically executed processes may be selected from one or more of:
1) transferring media, preferably enzyme media, into the disaggregation chamber (for example, in accordance with the sealable disaggregation flexible container of the kit of the invention). The media may be transferred into the disaggregation chamber, or in one embodiment also enters and collects enzymes prior to disaggregation using one or more embodiments of the invention, e.g. a mechanism such as weight sensors which will assess the required amount of media to add either determined by: direct operator input or weight of solid tissue. Incubating with the media at an optimal temperature of between 30 & 37° C. but could be as low as 0° C. up to 40° C. for at least 1 minute to several hours but more preferable 15 to 45 minutes.

2) undertaking physical disaggregation for a minimum of a few seconds up to several hours with an optimal time of between 1 and 10 minutes required to break up the solid tissue until there is no visual change (FIG. 5A). The disaggregation is designed to compress the tissues using a variable speed and time depending upon the time taken to disaggregate and feedback via sensors within the disaggregation module.

Steps 1) or 2) may be repeated until the tissue stops changing or has been disaggregated into a liquid cell suspension (whichever comes 1st monitored by a sensor in the disaggregation module).

3) removing disaggregated tissues, associated material and impurities by passing the disaggregated tissue and media through one or more filters enabling optional enrichment of the cell suspension. Direct pass through one or more mechanical filters with holes at least >0.1 µm to 1000 µm but most preferably between 50 and 250 µm and more preferably 100 µm to 200 µm. Alternatively, other separation methods may be used such as:

I. density based separation using centrifugation and/or sedimentation with or without a cell aligned density retention solution (e.g. Ficoll-paque GE Healthcare).

II. Hydrodynamic filtration where fluid flow and flow obstructing materials enhance the resolution and fractionation of the cells and impurities based on size and shape III. Field flow fractionation where an applied field (e.g. flow, electric, gravitational, centrifugal) acts in a perpendicular or reverse direction to the selection flow (e.g. Tangential flow filtration, Hollow fibre flow filtration, Asymmetric flow filtration, Centrifugal flow filtration). In which case: cells or impurities which are most responsive to the force are driven to the wall where flow is lowest and therefore a long retention time; while cells or impurities which are least responsive to the force remain laminar to the flow and elute quickly (tangential flow filtration)

IV. Acoustophoresis where one or more an acoustic frequency(ies) tuned to or harmonized with populations of cells or impurities is used to drive the required cells or impurities in a tangential path to the input stream.

4. Re-suspending the disaggregated cell product in fresh or additional media. This could be a cell enrichment media in order to undergo an independent targeted enrichment procedure or direct cell culture or cold storage media (such as HypoThermosol° from BioLife Solutions).

5. Transferring to a stabilising module containers for storage for hours to days or 6. Re-suspending in, or addition of a, cryoprotectant—a freezing solution for storage of the disaggregated solid tissue derived product for days to years (such as CryoStor° Freezing solution from BioLife Solutions) and transferring to one or more flexible stabilising module having a cryopreservation container(s)

7. Performing a controlled rate freezing process

8. Separating the aseptic processing kit from the device for independent storage or distribution.

During such steps it is apparent that the disaggregated module and the storage module may comprise one and the same flexible container, for receiving the sample and storing the sample and a further flexible container for housing the media for disaggregation. In some embodiments the same flexible containers are part of different modules of the kit.

BRIEF DESCRIPTION OF THE FIGURES

FIG. 3A (also referred to herein as FIG. 3a or FIG. 3a, and the like) depicts an embodiment of the subject matter described herein.

FIG. 5B (also referred to herein as FIG. 5B, and the like) reports data on tissue size versus disaggregation time, incubation and volume in a 100 mL fill flexible container.

DETAILED DESCRIPTION

Figure 1:
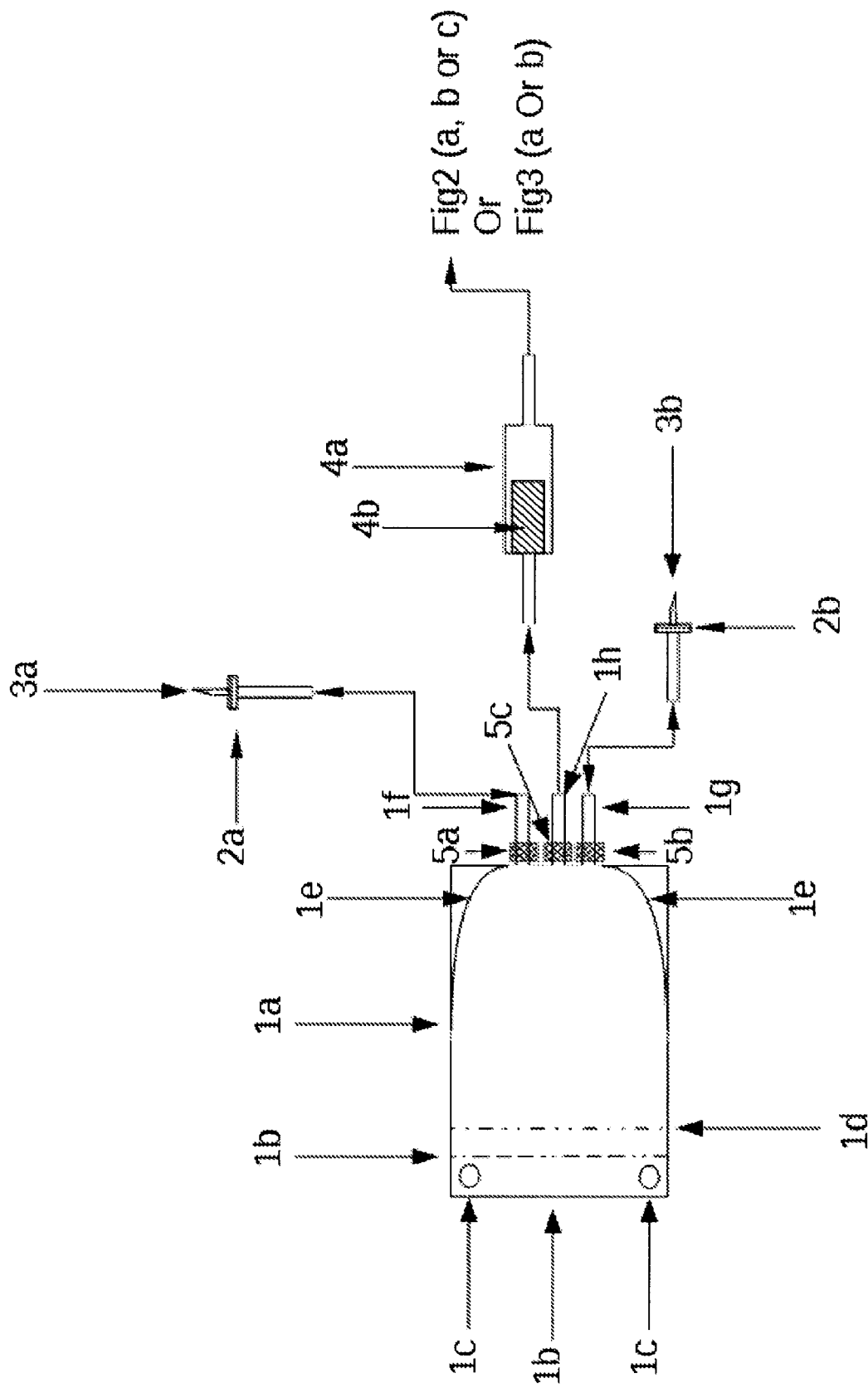
FIG. 1 (also referred to herein as FIG. 1, FIG. 1 or FIG. 1, and the like) depicts an embodiment of the subject matter described herein.

The processing of tissue to cells according to the kit, semi-automated device and methods of present disclosure are described further in the accompanying examples and figures numbered 1 to 7.

Moreover, by utilising the kit, device and processes described herein, in conjunction with ordinary skills in the art, further embodiments of the present disclosure can be readily identified. Those skilled in the art will readily understand known variations.

Definitions of the Disclosure

Unless defined otherwise, technical and scientific terms used herein have the same meaning as commonly understood by one of ordinary skill in the art to which this invention belongs. "depletion" as used herein refers to a process of a negative selection that separates the desired cells from the undesired cells which are labelled by one marker-binding fragment coupled to a solid phase.

"disaggregation or disaggregate" as used herein refers to the transformation of solid tissue into a single cells or small cell number aggregates where a single cell as a spheroid has a diameter in the range of 5 µm, 6 µm, 7 µm, 8 µm, 9 µm, 10 µm, 20 µm, 30 µm, 40 µm, 50 µm, 60 µm, 70 µm, 80 µm, 90 µm, 100 µm or more where this is more usually between 7 to 20 µm.

"cellularised or cellularisation" as used herein refers to the process of disaggregation where by the solid tissue a multicellular material generally made up of multiple cell lineages/types is broken down into small numbers of cells including but not limited to one cell but could be multiple cells of various lineages or cell types in very small numbers i.e. clump of cells or cell aggregates.

"engineered" as used herein refers to either addition of nucleic material or factors which change the tissue derived cell function from their original function to have a new or improved function for its ultimate utility.

"filtrate" as used herein refers to the material that passes through a filter, mesh or membrane.

"flexible container" as used herein refers to a flexible packaging system in multiple formats with one or more different types of film. Each film type is selected to provide specific characteristics to preserve the physical, chemical, and functional characteristics of the sterile fluids, solid tissue derived cellular material and the container integrity depending upon the step of the process.

"freezing solution" or "cryopreservation solution" also referred in the field to as the cryoprotectant is a solution that contains cryoprotective additives. These are generally permeable, non-toxic compounds which modify the physical stresses cells are exposed to during freezing in order to minimise freeze damage (i.e. due to ice formation). Most commonly a % Vol/Vol of one or more of the following: Dimethylsulphoxide (DMSO); Ethylene glycol; Glycerol; 2-Methyl-2,4-pentanediol (MPD); Propylene glycol; Sucrose; & Treha lose.

"media" means various solutions known in the art of cell culturing, cell handling and stabilisation used to reduce cell death, including but not limited to one or more of the following media Organ Preservation Solutions, selective lysis solutions, PBS, DMEM, HBSS, DPBS, RPMI, lscove's medium, XVIVO™, Lactated Ringer's solution, Ringer's acetate, saline, PLASMALYTE™ solution, crystalloid solutions and IV fluids, colloid solutions and IV fluids, five percent dextrose in water (D5W), Hartmann's Solution. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cell expansion). The media may have supplements or reagents well known in the art, e.g. albumins and transport proteins, amino acids and vitamins, antibiotics, attachments factors, growth factors and cytokines, hormones, metabolic inhibitors or solubilising agents. Various media are commercially available e. g. from ThermoFisher Scientific or Sigma-Aldrich.

"non-labelled" or "untouched" as used herein refers to the cells which are not bound by one marker-binding fragment coupled to a solid phase. The non-labelled, untouched cell fraction contains the desired target cells.

"non-target cells" as used herein refers to cells which are specifically bound by one marker-binding fragment which is coupled to a solid phase that is used to remove an unwanted cell type.

"positively separated" as used herein refers to the active separation of cells which are bound by one marker-binding fragment coupled to a solid phase and these cells are the required population of cells.

"negatively separated" as used herein refers to the active separation of cells which are bound by one marker-binding fragment coupled to a solid phase and these cells are not the required population of cells.

"purity" as used herein refers to the percentage of the target population or populations desired from the original solid tissue.

"regenerative medicine(s)", "adoptive cell therapy(ies)" or "advanced therapy medicinal product(s)" are used interchangeably herein to refer to cellular material that is used for therapeutic purposes of one or more mammals either by: the action of a part of or all of the cellular material; the supportive actions of a part of or all of the cellular material with the aim to improve the wellbeing of the mammal after application. The therapeutic cells can either be used directly or may require further processing, expansion and/or engineering to provide these actions.

"sample" as used herein refers to a sample containing cells in any ratio. Preferentially, these cells are viable. But, these cells can also be fixed or frozen cells which may be used for subsequent nucleic acids or protein extraction. The samples may be from animals, especially mammals such as mouse, rats or humans. Any compressible solid tissue that contains cells can be used. The invention is illustrated mainly through the isolation of hematopoietic and cancer cells from solid tumour tissue. However, the invention relates to a method for isolation of a breadth of cells from any mammalian solid tissue.

"marker" as used herein refers to a cell antigen that is specifically expressed by a certain cell type. Preferentially, the marker is a cell surface marker, so that enrichment, isolation and/or detection of living cells can be performed.

"solid phase" as used herein refers to the coupling of the marker-binding fragment, e.g. an antibody, bound to another substrate(s), e.g. particles, fluorophores, haptens like biotin, polymers, or larger surfaces such as culture dishes and microtiterplates. In some cases the coupling results in direct immobilization of the antigen-binding fragment, e.g. if the antigen-binding fragment is coupled to a larger surface of a culture dish. In other cases this coupling results in indirect immobilisation, e.g. an antigen-binding fragment coupled directly or indirectly (via e.g. biotin) to a magnetic bead is immobilised if said bead is retained in a magnetic field. In further cases the coupling of the antigen-binding fragment to other molecules results not in a direct or indirect immobilization but allows for enrichment, separation, isolation, and detection of cells according to the present invention, e.g. if the marker-binding fragment is coupled to a chemical or physical moiety which then allows discrimination of labelled cells and non-labelled cells, e.g. via flow cytometry methods, like FACSsorting, or fluorescence microscopy.

"solid tissue" as used herein refers to a piece or pieces of animal derived mammalian solid tissue which by its three dimensions i.e. length, breadth and thickness as a geometrical body is larger than the size of multiple individual cell based units and often contains connective materials such as collagen or a similar matrix that make up structure of the tissue whereby said solid tissue cannot flow through tubes or be collected by a syringe or similar small conduit or receptacle and is i.e. with dimensions in the range of 500 µxn, 1 mm, 2 mm, 3 mm, 4 mm, 5 mm, 1 cm, 2 cm, 3 cm, 4 cm, 5 cm, 10 cm, 20 cm, 30 cm or more "particle" as used herein refers to a solid phase such as colloidal particles, microspheres, nanoparticles, or beads. Methods for generation of such particles are well known in the field of the art. The particles may be magnetic particles or have other selective properties. The particles may be in a solution or suspension or they may be in a lyophilised state prior to use in the present invention. The lyophilized particle is then reconstituted in convenient buffer before contacting the sample to be processed regarding the present invention.

"magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

"marker-binding fragment" as used herein refers to any moiety that binds preferentially to the desired target molecule of the cell, i.e. the antigen. The term moiety comprises, e.g., an antibody or antibody fragment. The term "antibody" as used herein refers to polyclonal or monoclonal antibodies which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labelled antibodies). The term "antibody" comprises both intact molecules and antibody fragments, such as Fab, Fab', F(ab')2, Fv and single-chain antibodies. Additionally, the term "marker-binding fragment" includes any moiety other than antibodies or antibody fragments that binds preferentially to the desired target molecule of the cell. Suitable moieties include, without limitation, oligonucleotides known as aptamers that bind to desired target molecules (Hermann and Pantel, 2000: Science 289: 820-825), carbohydrates, lectins or any other antigen binding protein (e.g. receptor-ligand interaction).

"retentate" as used herein refers to the material that does not pass through a filter, mesh or membrane.

"ultimate utility" as used herein refers to manufacture of or direct use in regenerative medicines, adoptive cell therapies, ATMPs, diagnostic in vitro studies or scientific research.

With reference to FIG. 1 there is disclosed:
1a Flexible container for: disaggregation; and digestion in the embodiment involving enzymatic digestion.
1b Open end for transfer of solid tissue materials into container 1a
1c hanging holes to support container 1a
1d target heat weld location to seal container 1a using heat welder 13m
1e rounded edges on internal container 1a surfaces to reduce losses which may occur as part of transfer to examples illustrated in FIG. 2 (a, b or c) or FIG. 3 (a or b)
1f tubing 1f enables media 3a to be transferred into container 1a via sterile filter 2a
1g in example tubing 1g enables digestion enzymes 3b to be transferred into container 1a via sterile filter 2b 1h after disaggregation, especially involving enzymatic digestion a phase of incubation, the mixture is transferred out via tubing 1h via filter unit 4a containing filter 4b prior to entering
2a spike and sterile filter for media 3a
2b spike and sterile filter for enzymes 3b in one example, where enzymes are required
3a media for disaggregation and in one example enzymatic digestion
3b enzymes for disaggregation in one example
4a flexible filter unit
4b non-disaggregated tissue filter
5a tubing clamp to allow media (3a) to enter the flexible container 1a via filter 2a
5b in one example where enzymes are used a tubing clamp will allow enzymes (3b) to enter the flexible container 1a via filter 2b
5c tubing clamp to allow contents of flexible container 1a to pass via filter 4a into one or more examples identified in FIG. 2 (a-c) Or FIG. 3 (a or b)

Figure 2A:
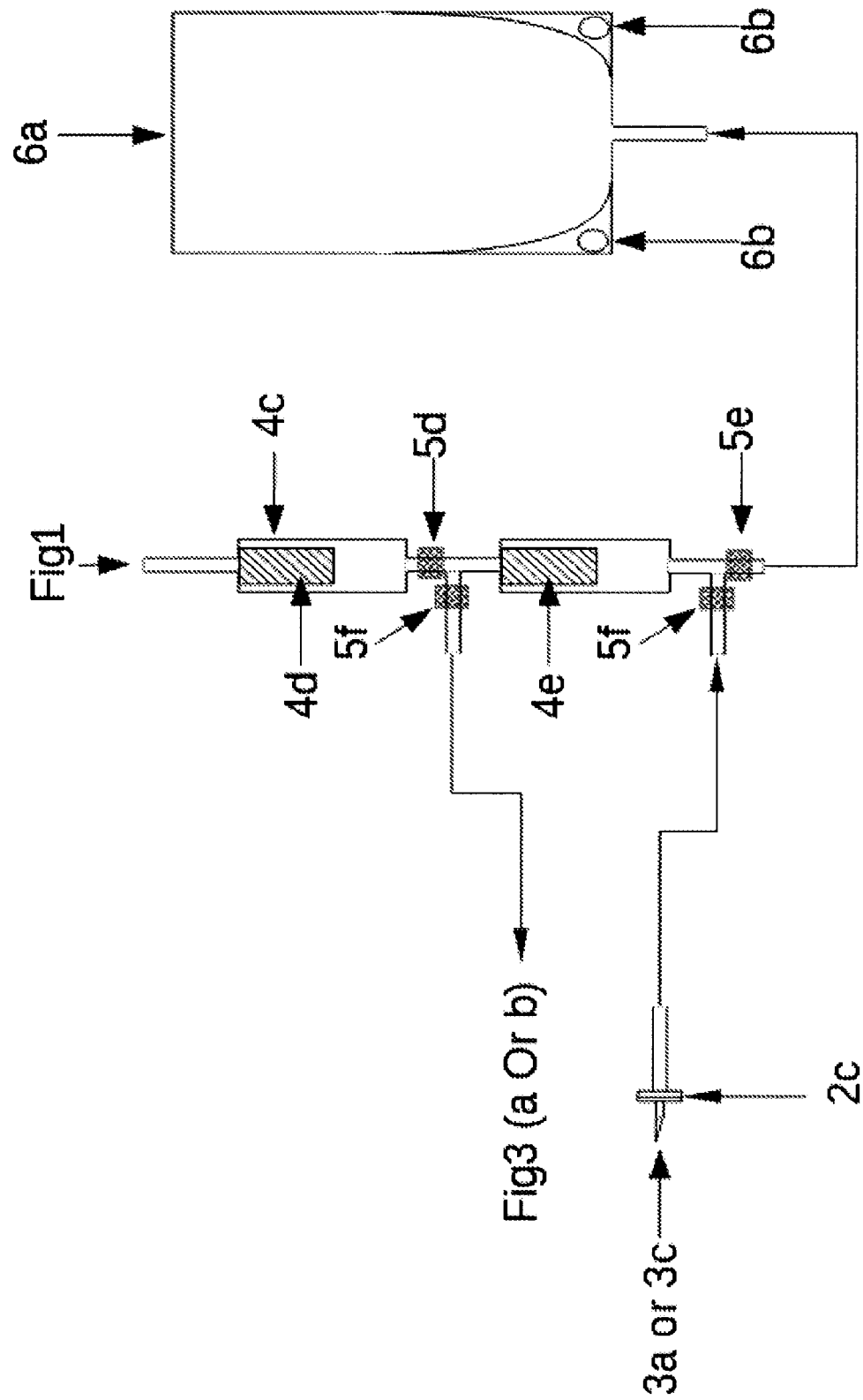
FIG. 2A (also referred to herein as FIG. 2a, FIG. 2a or FIG. 2a, and the like) depicts an embodiment of the subject matter described herein.
Figure 2B:
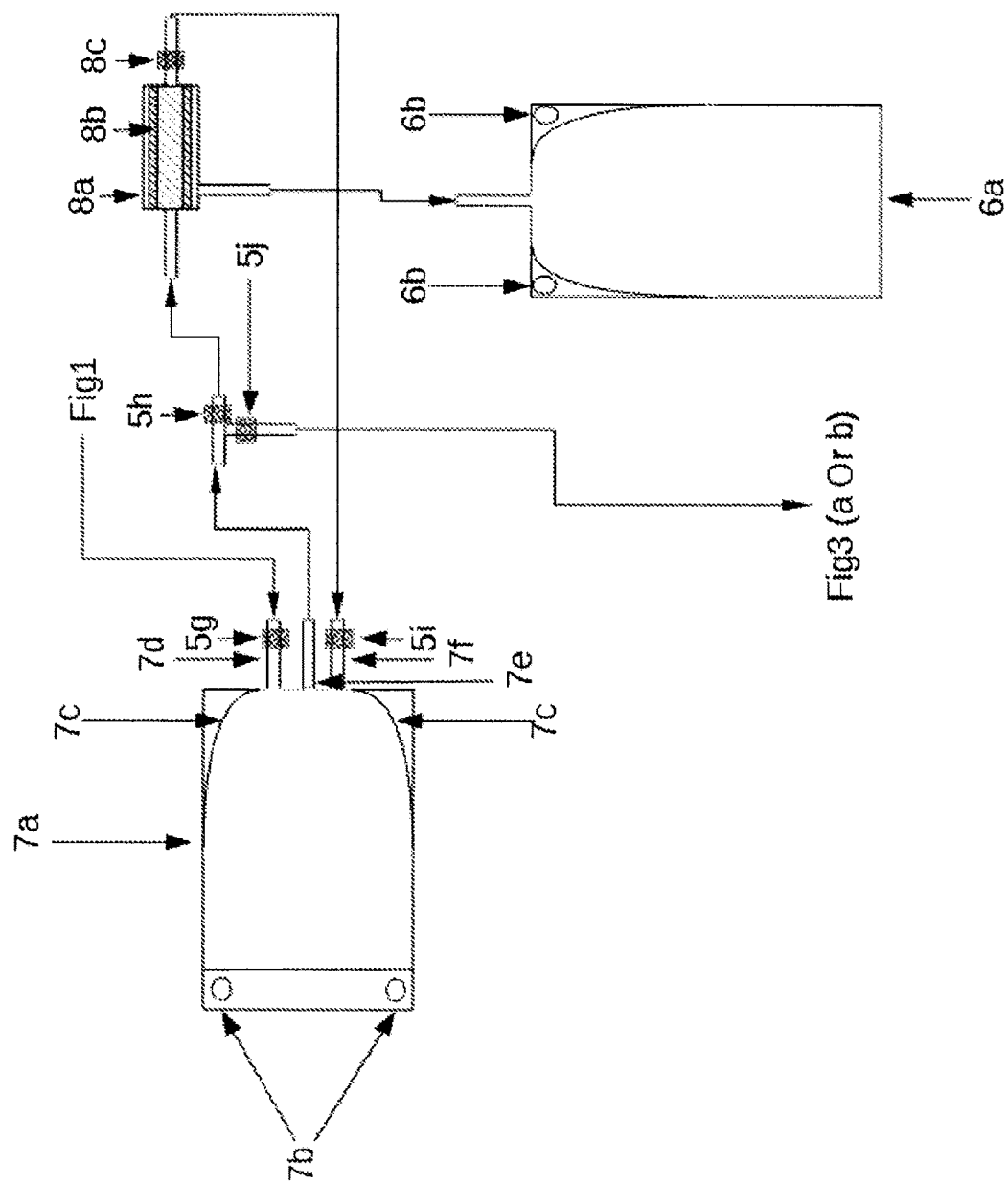
FIG. 2B (also referred to herein as FIG. 2b, FIG. 2b or FIG. 2b, and the like) depicts an embodiment of the subject matter described herein.
Figure 3B:
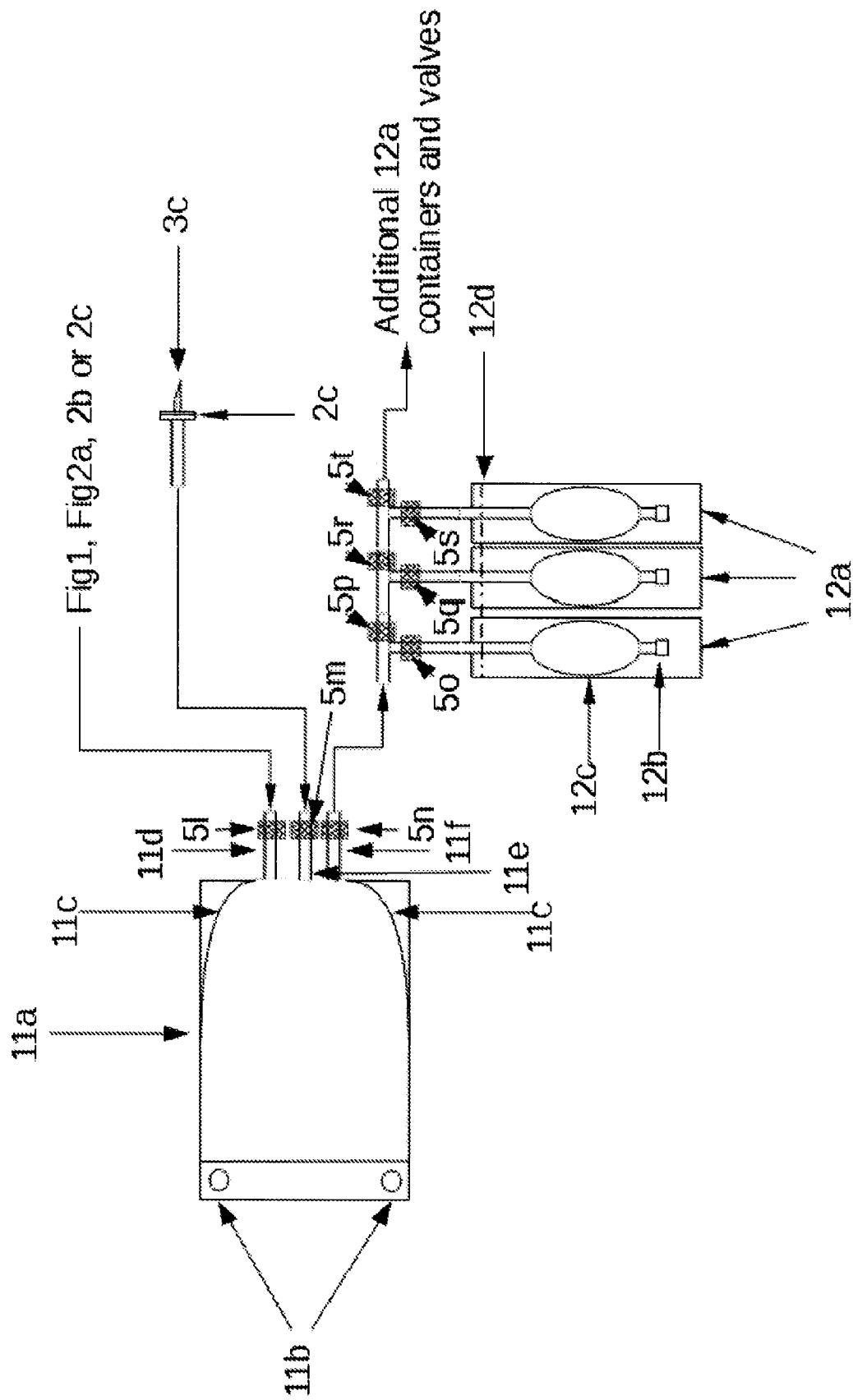
FIG. 3B (also referred to herein as FIG. 3b or FIG. 3b, and the like) depicts an embodiment of the subject matter described herein.

FIG. 2a provides a further example of the invention in which:
2c spike and sterile filter for media
3a in one example short term storage media
3c freezing solution a media required for cryopreservation in one of the examples illustrated in FIG. 2a or FIG. 3b
4c in one example an additional flexible filter module containing filters 4d & 4e
4d in one example FIG. 2a a flexible filter unit may be required for additional size segregation of cell/tissue clumps
4e in one example FIG. 2a a flexible filter unit is required to retain cells but allow the media/cell fragments to be washed out
5d in one example FIG. 2a tubing clamp is in place to stop material from container 1a that has passed though 4a & 4c from returning back to container 1a
5e in one example FIG. 2a tubing clamp is in place to allow waste material from container 1a that has passed through 4a, 4c and 4e to enter container 6a but stop media (3a or 3c) entering via filter 2c from entering container 6a
5f both tubing clamps stop material from container 1a that has passed though filters 4a, 4c and 4e from entering the tubing to the media container (3a or 3c) or transferring to one of the examples FIG. 3 (a or b) before the waste has passed into container 6a via 5e. Once the waste has been depleted then tubing clamps 5e and 5d close and both tubing clamps 5f allowing media (3a or 3c) to transfer cells within filter 4e into one of the examples identified in FIG. 3 (a or b)
6a a waste container
6b hanging holes to support container 6a FIG. 2b provides yet a further example in which:
5g a tubing clamp in place to allow contents of container 1a to enter the flexible container 7a via filter 4a
5h a tubing clamp in place to allow contents of container 7a to pass through filter 8a retaining and enriching for cells while allowing waste and debris to pass through filter 8b into container 6a with the pressure controlled by valve 8c before the enriched cells return to container 7a via an open clamp 5i
5i a tubing clamp is in place to allow contents of container 7a via open tubing clamp 5h to pass through filter 8a retaining and enriching for cells while allowing waste and debris to pass through filter 8b into container 6a with the pressure controlled by valve 8c before the enriched cells return to container 7a

5j after cell enrichment has occurred then tubing clamp 5h closes and 5j opens allowing contents of 7a to pass on to one of the examples FIG. 3 (*a* or *b*)

6a a waste container

6b hanging holes to support container 6a

7a a flexible container to receive the contents of: 1a via filter 4a; and filter 8a

7b hanging holes to support container 7a

7c rounded edges on internal container 7a to reduce losses which may occur as part of transfer to examples illustrated in FIG. 3 (*a* or *b*)

7d tubing to allow container 7a to receive the contents of: 1a via filter 4a; and filter 8a

7e tubing to allow contents of container 7a to pass through filter 8a retaining and enriching for cells while allowing waste and debris to pass through filter 8b into container 6a with the pressure controlled by valve 8c before the enriched cells return to container 7a via an open clamp 5i

7f tubing to allow contents of container 7a via open tubing clamp 5h to pass through filter 8a retaining and enriching for cells while allowing waste and debris to pass through filter 8b into container 6a with the pressure controlled by valve 8c before the enriched cells return to container 7a

8a contents of container 7a can be filtered to remove waste media and debris via filter

8b while enriching for cells under the control of valve 8c before returning to container 7a

8b & 8c see 8a

Figure 2C:
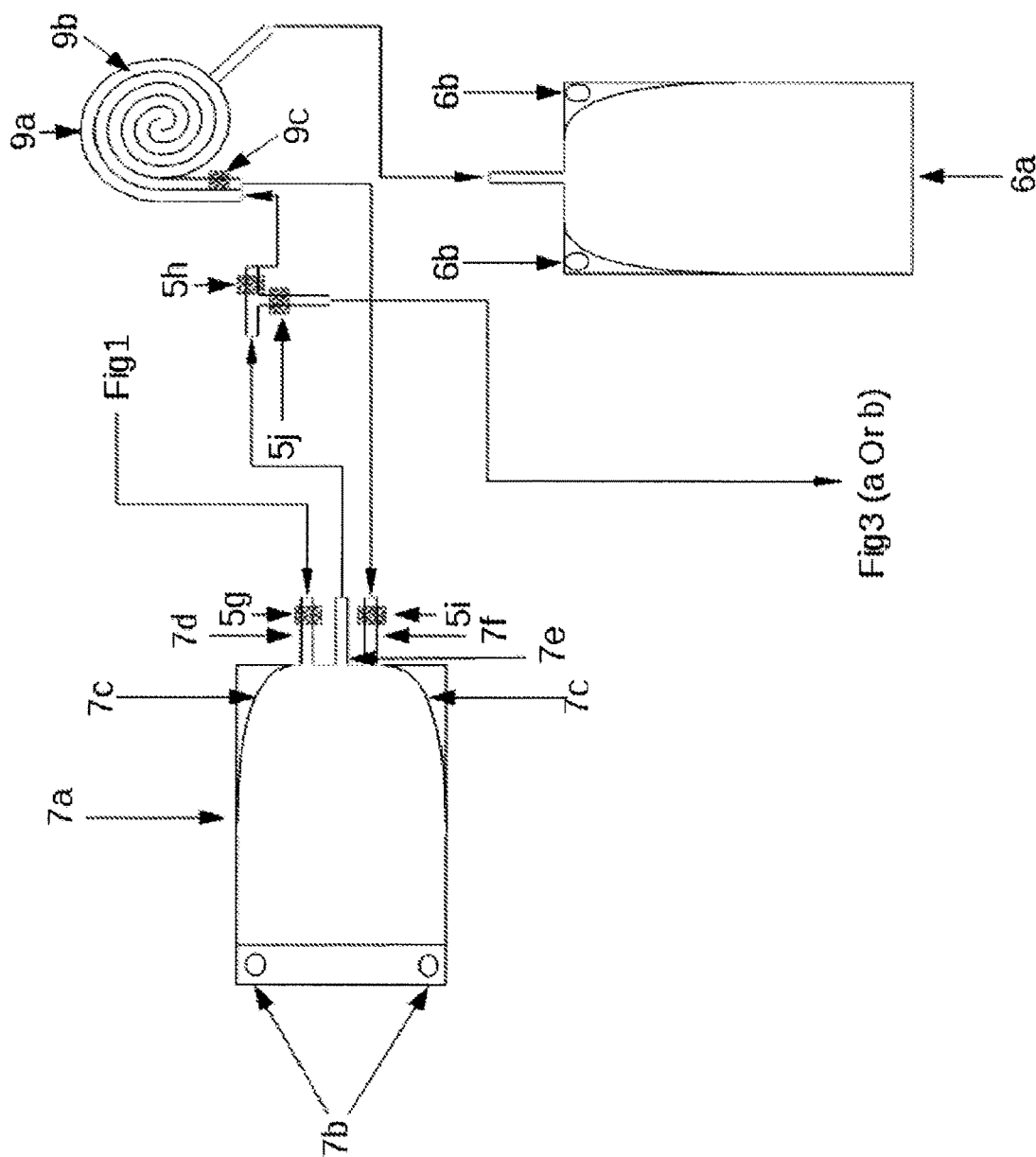
FIG. 2C (also referred to herein as FIG. 2c, FIG. 2c or FIG. 2c, and the like) depicts an embodiment of the subject matter described herein.

In one example, as shown in FIG. 2c it is described that

5g a tubing clamp in place to allow contents of container 1a to enter the flexible container 7a via filter 4a

5h a tubing clamp in place to allow contents of container 7a to pass through filter 9a retaining and enriching for cells while allowing waste and debris to pass through filter 9b into container 6a with the pressure controlled by valve 9c before the enriched cells return to container 7a via an open clamp 5i

5i a tubing clamp is in place to allow contents of container 7a via open tubing clamp 5h to pass through filter 9a retaining and enriching for cells while allowing waste and debris to pass through filter 9b into container 6a with the pressure controlled by valve 9c before the enriched cells return to container 7a

5j after cell enrichment has occurred then tubing clamp 5h closes and 5j opens allowing contents of 7a to pass on to one of the examples FIG. 3 (*a* or *b*)

6a a waste container

6b hanging holes to support container 6a

7a a flexible container to receive the contents of: 1a via filter 4a; and filter 9a

7b hanging holes to support container 7a

7c rounded edges on internal container 7a to reduce losses which may occur as part of transfer to examples illustrated in FIG. 3 (*a* or *b*)

7d tubing to allow container 7a to receive the contents of: 1a via filter 4a; and filter 9a

7e tubing to allow contents of container 7a to pass through filter 9a retaining and enriching for cells while allowing waste and debris to pass through filter 9b into container 6a with the pressure controlled by valve 9c before the enriched cells return to container 7a via an open clamp 5i

7f tubing to allow contents of container 7a via open tubing clamp 5h to pass through filter 9a retaining and enriching for cells while allowing waste and debris to pass through filter 9b into container 6a with the pressure controlled by valve 9c before the enriched cells return to container 7a

9a contents of container 7a can be filtered to remove waste media and debris via filter 9b while enriching for cells under the control of valve 9c before returning to container 7a

9b & 9c see 9a

FIG. 3a provides yet a further example of the invention in which:

5k a tubing clamp is in place to allow the contents of: 1a (in example FIG. 1 via filter 4a or in example FIG. 2a via filter 4c); or 7a (in example FIG. 2b via filter 8a or in example FIG. 2c via filter 9a) to be transferred into container 10a

10a a flexible container to receive the contents of: 1a via filter 4a (in example FIG. 1) where examples described in FIG. 2 (*a, b* or *c*) are not required; 1a via filters 4a & 4c (in example FIG. 2a); 7a via filter 8a (in example FIG. 2b); or 7a via filter 9a (in example FIG. 2c)

10b hanging holes to support container 10a

10c rounded edges on internal container 10a to reduce losses which may occur as part of transfer out via 10e or *f*

10d tubing to enable container 10a to receive the contents of: 1a via filter 4a (in example FIG. 1) where examples described in FIG. 2 (*a, b* or *c*) are not required; 1a via filters 4a & 4c (in example FIG. 2a); 7a via filter 8a (in example FIG. 2b); or 7a via filter 9a (in example FIG. 2c)

10e tubing to enable contents of container 10a to be withdrawn via connector 10h

10f tubing with a flexible membrane to enable a sterile spike to be introduced via cover

10g to enable contents of container 10a to be withdrawn

10g aseptic cover for tubing containing membrane 10f

10h connector to enable contents of 10a to be withdrawn via tubing 10e

In a further example, as shown in FIG. 3b there is provided:

2c spike and sterile filter for media (3c)

3c media required for cryopreservation

5l tubing clamp to allow the contents of: 1a (in example FIG. 1 via filter 4a or in example FIG. 2a via filter 4c); or 7a (in example FIG. 2b via filter 8a or in example FIG. 2c via filter 9a) to be transferred into container 11a

5m tubing clamp to allow media (3c) to enter the flexible container 11a via filter and spike 2c

5n tubing clamp to allow contents of container 11a to enter one of the 12a containers depending on the open or closed status of tubing clamps 5o to 5t

5o-5t tubing clamps to allow contents of container 11a to enter one of the 12a containers depending on the open or closed status of tubing clamps 5o to 5t

11a a flexible container to receive the contents of: 1a via filter 4a (in example FIG. 1) where examples described in FIG. 2 (*a, b* or *c*) are not required; 1a via filters 4a & 4c (in example FIG. 2a); 7a via filter 8a (in example FIG. 2b); or 7a via filter 9a (in example FIG. 2c)

11b hanging holes to support container 11a

11c rounded edges on internal container 11a to reduce losses which may occur as part of transfer out via 11f

11*d* tubing to enable container 10*a* to receive the contents of: 1*a* via filter 4*a* (in example FIG. 1) where examples described in FIG. 2 (*a*, *b* or *c*) are not required; 1*a* via filters 4*a* & 4*c* (in example FIG. 2*a*); 7*a* via filter 8*a* (in example FIG. 2*b*); or 7*a* via filter 9*a* (in example FIG. 2*c*)

11*e* tubing to allow cryopreservation media 3*c* to be transferred into container 11*b*

11*f* tubing to enable the contents of 11*a* to be transferred to container(s) 12*a*

12*a* flexible containers to cryopreserve and store the final disaggregated cells product.

12*b* a fixture allowing aseptic transfer of the cells out of the container (12*a*)

12*c* a space as part of 12*a* suitable for the volume to be stored

12*d* a target location for welding the tubing and secondary flexible container as part of

12*a* using welder 13*n*

Figure 4:
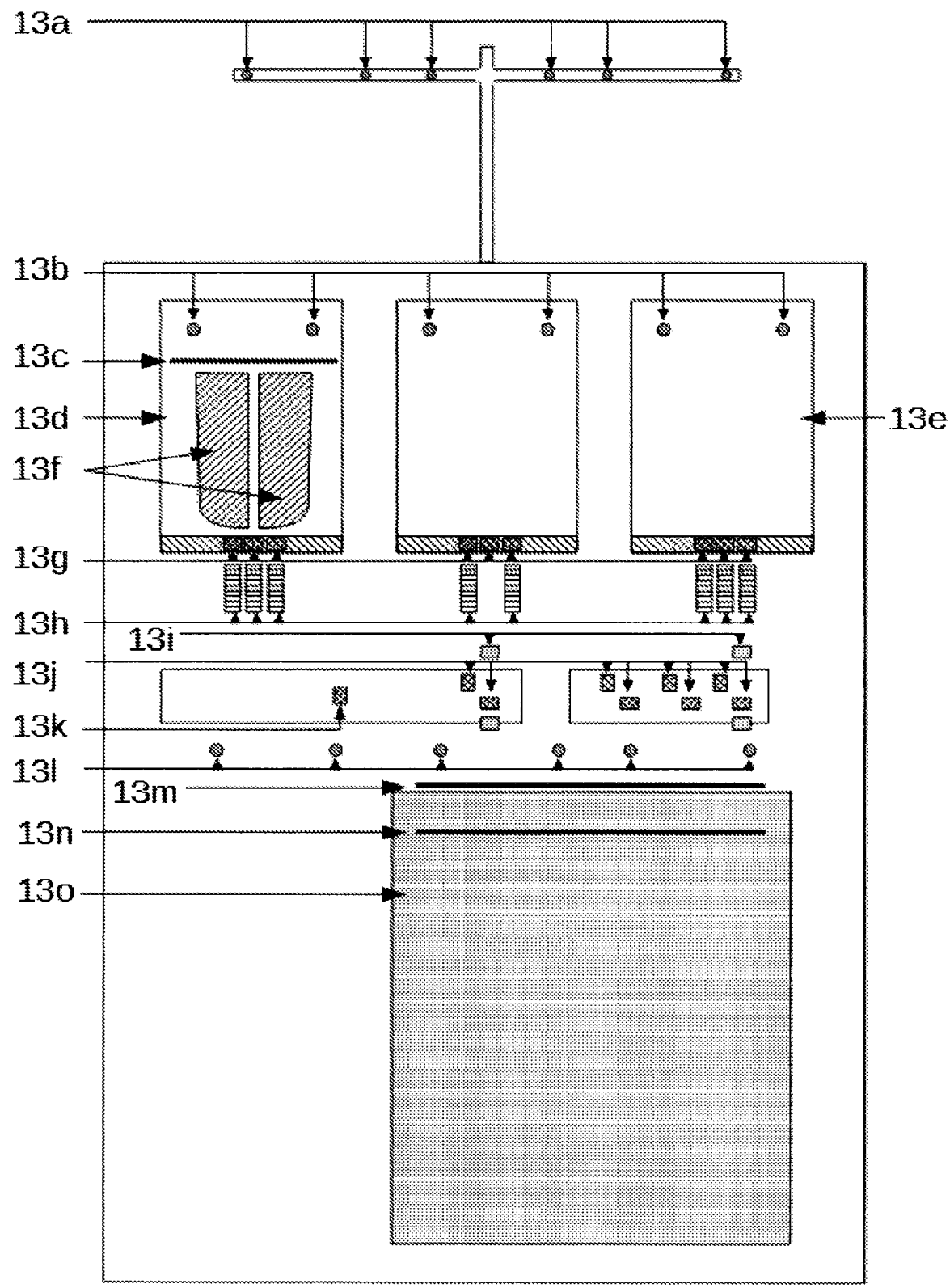
FIG. 4 (also referred to herein as FIG. 4, FIG. 4 or FIG. 4, and the like) depicts an embodiment of the subject matter described herein.

FIG. 4 shows a further example of the device and kit of the invention in which:

13*a* Pegs for hanging media 3*a*, 3*b*, 3*c*

13*b* pegs connected to weight sensors for hanging containers 1*a* and depending on the examples used these could include one or more of: 7*a*, 10*a* & 11*a*. Where the weight sensors are used to define decision stages to control the automated processing of the materials

13*c* Heat welder to seal container 1*a* at target site 1*d* after tissue has been introduced

13*d* disaggregation module with an opening that can be closed and locked to enable disaggregation and in the example that uses digest enzymes is capable of controlling temperatures between 0° C. and 40° C. to a tolerance of 1° C. to enable digestion. The module also has a built in sensor to assess the level of solid tissue disaggregation by determining the variation in light distribution against time to identify change and thereby identifying completion of the disaggregation process which will occur over a period of seconds to hours.

13*e* final formulation module with an enclosure to allow temperature control of either container 10*a* or 11*a* depending on the example used which is capable of controlling temperatures between 0° C. and ambient environmental temperature to a tolerance of 1° C.

13*f* disaggregation surfaces which come directly into contact with container 1*a* and pushes against the back of the module 13*d* enclosure which can be closed and locked during disaggregation and digestion where enzymes are utilised.

13*g* tubing clamp

13*j* tubing clamp

13*h* peristaltic tubing pumps

13*i* tubing locators

13*k* tubing valve required for examples FIGS. 2*b* & 2*c*

13*l* Pegs for hanging containers depending on the examples used these could include one or more of: 6*a* & 12*a*

13*m* tubing welder and cutter required for example FIG. 3*b* for tubing to container(s) 12*a*

13*n* tubing welder required for example FIG. 3*b* for tubing to container(s) 12*a* at target location 12*d*

13*o* controlled rate cooling module capable of cooling or maintaining any temperature between 8° C. and at least −80° C.

EXAMPLE METHOD

The method of the invention is exemplified according to the following process. It is clearly stated that other than the essential features of the method, the various optional steps listed herein can be independently combined to achieve the relevant technical advantages associated with the type of sampling and result to be achieved.

A semi-automatic aseptic tissue processing method comprising: automatically determining aseptic disaggregation tissue processing steps and one or more further tissue processing steps and their associated conditions from a digital tag identifier on an aseptic processing kit, optionally in accordance with the kit described herein; placing a tissue sample into a flexible plastic container of the aseptic processing kit; and processing the tissue sample by automatically executing the one or more tissue processing steps by communicating with and controlling the disaggregation module; the optional enrichment module; and the stabilisation module.

Essentially the process may comprise taking an open ended bag (1st flexible container that is part of disaggregation module) that will receive the biopsy/tissue sample which is already connected via one or more conduits to (conduit) or can be connected via a manual operator controlled aseptic connection to I. a single container with digestion media (2nd flexible container that is part of the disaggregation module) and with or without a stabilisation solution (same 2nd flexible container is part of the stabilisation module also)

II. one container with a digestion solution (2nd flexible container that is part of the disaggregation module) & another container with a stabilisation solution (4th flexible container is part of the stabilisation module) on addition of the biopsy and sealing of the open ended bag the digestion media can be added via the conduit or aseptic connections (conduit/ports claim 1) and the tissue material processed.

On completion of the digestion by which point the tissue is now a single or small number aggregate cellular suspension the cells can optionally be filtered prior to step 4 (optional enrichment module for filtration comprises the 1st flexible container containing sample and filtered to a 3rd container for receiving the enriched filtrate)

Where the stabilisation media is not present in the same flexible container i.e. option 2.11. this will require the container with stabilisation solution to be added by opening the attached conduit or manual operator controlled aseptically connection to be competed and said connection to be opened enabling in both cases the stabilisation solution to be added before the process continues.

The single or small number aggregate cellular suspension in the original flexible container or which may be optionally subdivided into multiple storage stabilisation containers thereafter are maintained in a stable state on the device and/or will undergo cryopreservation prior to removal for, transport, storage and or used in their ultimately utility. (The stabilisation module also comprises 1st or 3rd container as used in storage/freezing/storage)

In one further non-limiting example of the process:
a) Collection of tissue sample by a separate procedure such as biopsy's or surgery to collect the required tissue material (not part of the invention) is placed into the initial flexible plastic container (see FIG. 1—container 1*a*).
b) Media (see example FIG. 1—media 3*a*) is transferred into the disaggregation chamber, or in one example also enters and collects enzymes (see FIG. 1—enzymes 3*b*), prior to disaggregation using one or more of the following examples of the invention a mechanism such as weight sensors (see FIGS. 1-13b as part of module 13d) will assess the required amount of media to add either determined by: direct operator input or weight of solid tissue.

c) The single use flexible disaggregation container, solid tissue, media and in one example enzymes are combined during a physical disaggregation process for a minimum of a few seconds up to several hours with an optimal time of between 1 and 10 minutes required to break up the solid tissue until there is no visual change (FIG. 5B Table). The disaggregation device is designed to compress the tissues using a variable speed and time depending upon the time taken to disaggregate and feedback via sensors within the disaggregation module (see example FIG. 1—13d).

d) In one embodiment where enzymes are present this will require incubation periods at an optimal temperature of between 30 & 37° C. but could be as low as 0° C. up to 40° C. for at least 1 minute to several hours but more preferable 15 to 45 minutes.

e) Step c and in the embodiment where enzymes step d) can be repeated until the tissue stops changing or the see example has been disaggregated into a liquid cell suspension whichever comes 1st monitored by a sensor in the disaggregation module disaggregation module (FIG. 1—13d).

f) In one embodiment incompletely disaggregated tissues, associated material and impurities are removed enabling enrichment of the cell suspension by passing the disaggregated tissue and media using one or more of the following embodiments:
 i. Direct pass through one or more mechanical filters with holes at least >0.1 μm to 1000 μm but most preferably between 50 and 250 μm and more preferably 100 μm to 200 μm (illustrated in FIG. 2a)
 ii. Density based separation using centrifugation and/or sedimentation with or without a cell aligned density retention solution (e.g. Ficoll-paque GE Healthcare).
 iii. Hydrodynamic filtration where fluid flow and flow obstructing materials enhance the resolution and fractionation of the cells and impurities based on size and shape
 iv. Field flow fractionation where an applied field (e.g. flow, electric, gravitational, centrifugal) acts in a perpendicular or reverse direction to the selection flow (e.g. Tangential flow filtration, Hollow fibre flow filtration, Asymmetric flow filtration, Centrifugal flow filtration). In which case: cells or impurities which are most responsive to the force are driven to the wall where flow is lowest and therefore a long retention time; while cells or impurities which are least responsive to the force remain laminar to the flow and elute quickly (tangential flow filtration illustrated in FIGS. 2b & c)
 v. Acoustophoresis where one or more an acoustic frequency(ies) tuned to or harmonized with populations of cells or impurities is used to drive the required cells or impurities in a tangential path to the input stream.

g) In one embodiment the disaggregated enriched tissue product will be resuspended in a fresh media (FIG. 2a using media 3a) such as:
 i. a cell enrichment media in order to undergo an independent targeted enrichment procedure as described previously
 ii. direct cell culture or cold storage media (such as HypoThermosol° from BioLife Solutions.

h) in the embodiment employed in g) the resuspended disaggregated solid tissue derived product will be transferred to one of the embodiment final product containers (illustrated in FIG. 3a) for storage for hours to days prior to being used for its ultimate utility.

i) otherwise after step f) the embodiment (illustrated in FIG. 3b) will apply where the disaggregated solid tissue derived product will undergo re-suspension in a cryoprotectant (FIG. 3b-media 3c) a freezing solution for storage of the disaggregated solid tissue derived product for days to years such as CryoStor° Freezing solution from BioLife Solution.

j) At this stage the disaggregated solid tissue derived product re-suspended in freezing solution using the device (FIG. 4—module 13e) will be transferred to 1 or more flexible cryopreservation container(s) (illustrated in FIG. 3a—container 12a) and in one embodiment of the device it will perform a controlled rate freezing process using the device (FIG. 4—module 13o).

k) After which the bags can be separated from the device and aseptic processing kit for independent storage or distribution.

Figure 6:
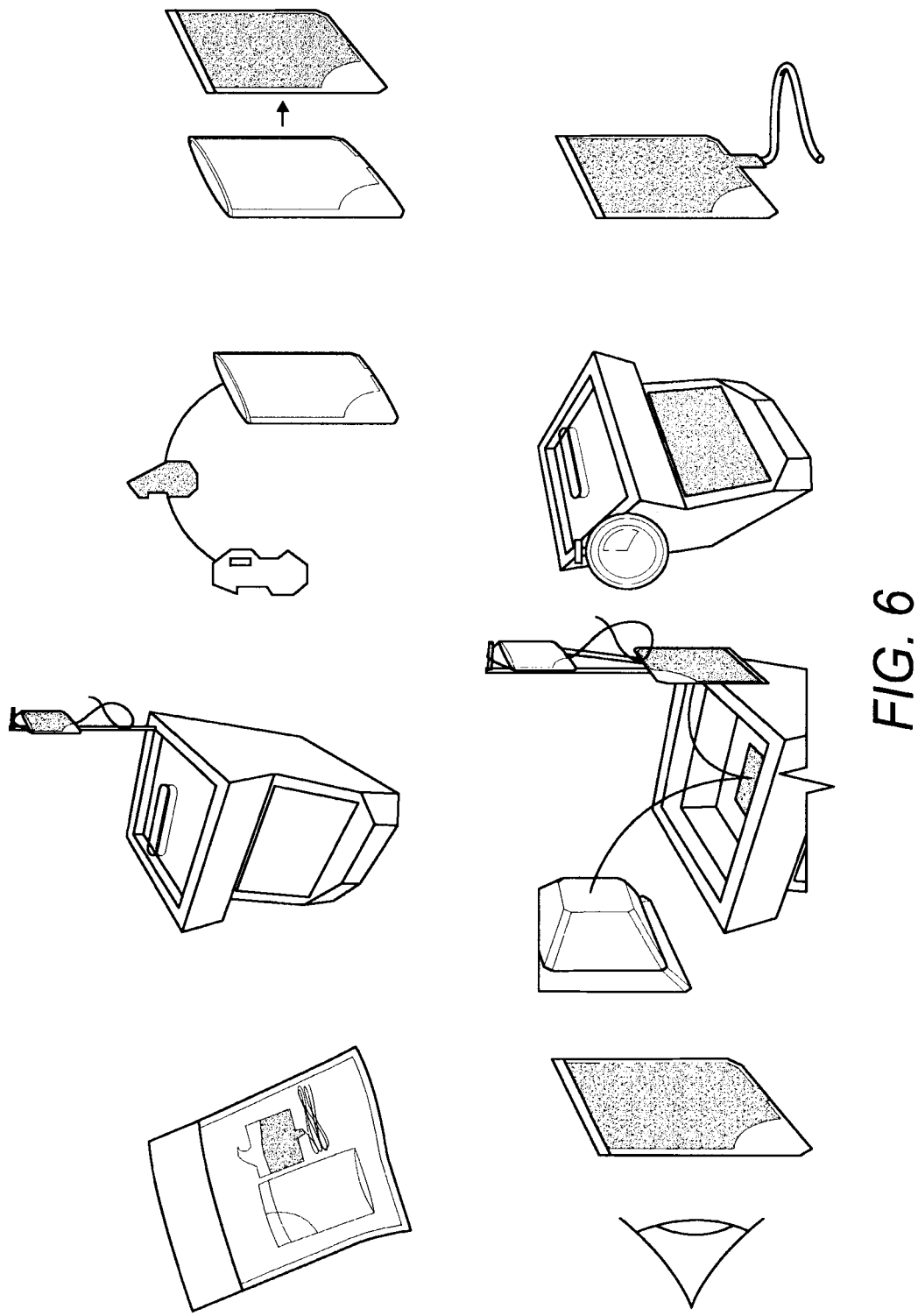
FIG. 6 (also referred to herein as FIG. 6, and the like) depicts an embodiment of the subject matter described herein.
Figure 7:
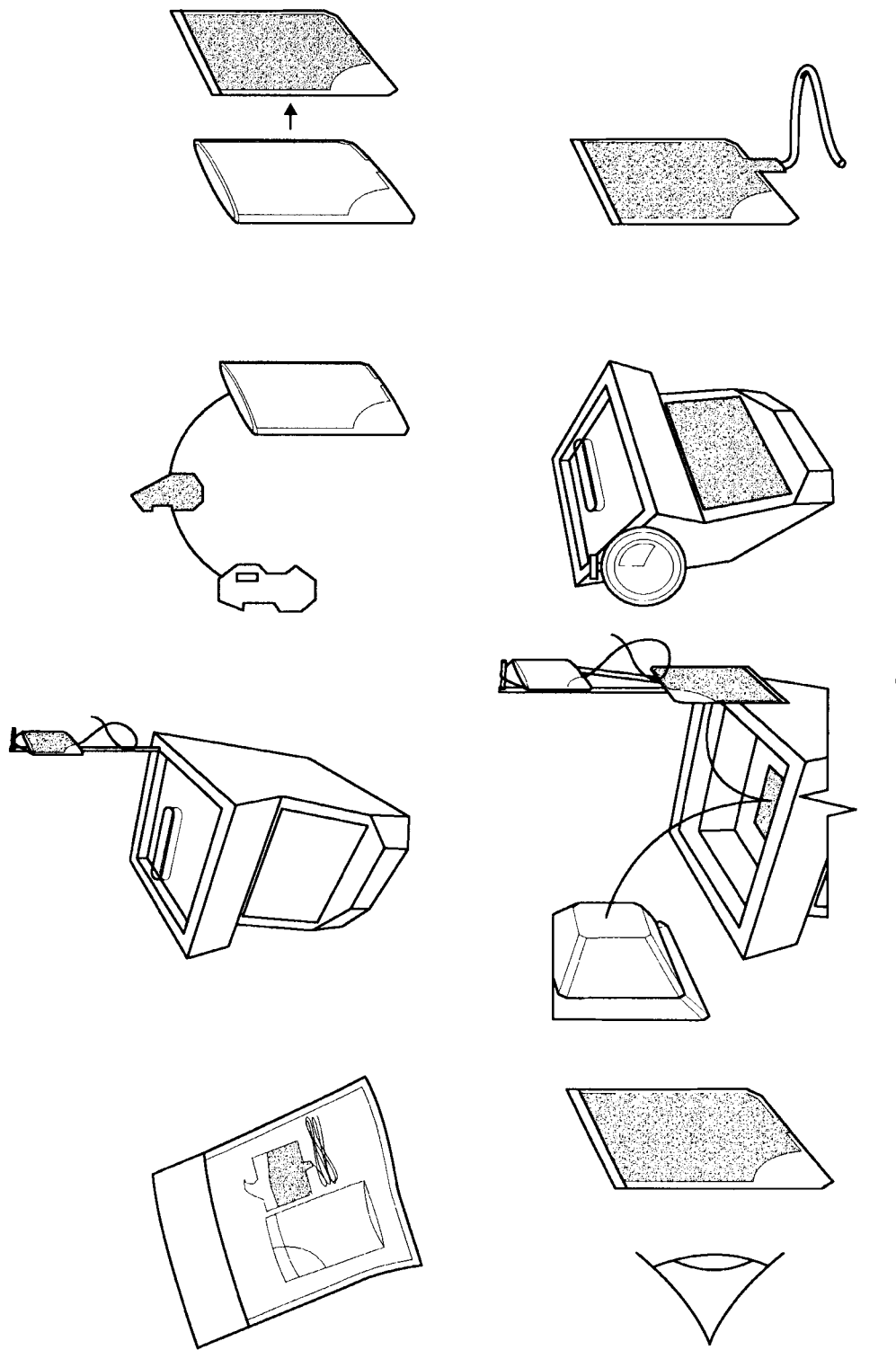
FIG. 7 (also referred to herein as FIG. 7, and the like) depicts an embodiment of the subject matter described herein.

FIGS. 6 and 7 describe further examples in which the disposable kit of the invention can be used with an automatic device for semi-automatic aseptic processing of tissue samples.

FIG. 6 describes the following semi-automatic aseptic tissue processing method using multiple flexible containers for different starting solutions that are part of the modules of the process used for disaggregation and stabilisation.

Process step 1—The user may login to device and scan the tag on the aseptic kit using the device to transfer the automatic processing steps to be used. The device processor recognises the tag and is provided with information needed to carry out the specific processing instructions related to that particular kit.

Process step 2—The digestion media containing flexible bag (part of disaggregation module) and cryo/stabilisation solution containing flexible bag (part of the stabilisation module) are each hung or secured to the device.

Process step 3—The biopsy or tissue sample for processing may be placed into a flexible container (part of both modules) of the aseptic kit via an open end.

Process step 4—The flexible container comprising the sample may then be sealed using a heat weld to close the open end (used to add the sample during initial processing).

Process step 5—The user may then interact with the user interface of the processor to confirm the tissue sample is present and enter any further tissue material specific information, if required.

Process step 6—Digestion media and cryo/stabilisation solution flexible containers are connected with the flexible container housing the sample, after which it may be placed into the device for automatic processing.

Process step 7—The device executes the cycles according to the kit information undertaking disaggregation of the sample and stabilisation/cryo preservation of resulting cells.

Process step 8—When stabilised/frozen disconnect and discard used media and cryo/stabilisation containers of kit. Tissue processed into single or multi-cell solution in flexible container is disconnected before transferring into storage or transport container prior to its ultimate utilisation.

FIG. 7 describes how flexible containers comprising the media used in the process may be shared between the modules of the aseptic processing kit and method.

Process step 1—The user may login to device and scan the tag on the aseptic kit using the device to transfer the automatic processing steps to be used.

Process step 2—A flexible bag (part of disaggregation/stabilisation module) comprising both the media and cryo/stabilisation solution is hung or otherwise secured to the device.

Process step 3—The biopsy or tissue sample for processing may be placed into a further flexible container (part of both modules) of the aseptic kit via an open end.

Process step 4—The flexible container comprising the sample may then be sealed using a heat weld to close the open end.

Process step 5—The user may then interact with the user interface of the processor to confirm the tissue sample is present and enter any tissue material specific information, if required.

Process step 6—Digestion media and cryo/stabilisation solution flexible container is connected with the flexible container housing the sample, after which it may be placed into the device for automatic processing.

Process step 7—The device cycles to enable disaggregation of the sample and stabilisation of resulting cells, optionally via cryopreservation.

Process step 8—When freezing/stabilising is complete the user disconnects and discard used flexible containers of kit. Tissue processed into single or multi-cell solution in the remaining flexible container is disconnected before transferring into storage or transport container prior to its ultimate utilisation.

Enzymatic Digestion

By way of example, in another embodiment of the method of the invention, where the disaggregation process is being supplemented with enzymatic digestion the media formulation for enzymatic digestion must be supplemented with enzymes that aid in protein breakdown causing the cell to cell boundaries to breakdown as described above.

Media Formulation for Enzymatic Digestion

Various liquid formulations known in the art of cell culturing or cell handling can be used as the liquid formulation used for cell disaggregation and enzymatic digestion of solid tissues, including but not limited to one or more of the following media Organ Preservation Solutions, selective lysis solutions, PBS, DMEM, HBSS, DPBS, RPMI, Iscove's medium, X-VIVO™, AIM-VT™, Lactated Ringer's solution, Ringer's acetate, saline, PLASMALYTE™ solution, crystalloid solutions and IV fluids, colloid solutions and IV fluids, five percent dextrose in water (D5W), Hartmann's SolutionDMEM, HBSS, DPBS, RPMI, AIM-VT", Iscove's medium, X-VIVO™, each can be optionally supplemented with additional cell supporting factors e.g. with foetal calf serum, human serum or serum substitutes or other nutrients or Cytokines to aid in cell recovery and survival or specific cell depletion. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cells). The media may have supplements or reagents well known in the art, e.g. albumins and transport proteins, amino acids and vitamins, metal-ion(s), antibiotics, attachments factors, de-attachment factors, surfactants, growth factors and cytokines, hormones or solubilising agents. Various media are commercially available e. g. from ThermoFisher, Lonza or Sigma-Aldrich or similar media manufacturers and suppliers.

The liquid formulation required for enzymatic digestion must have sufficient calcium ions present in the of at least 0.1 mM up to 50 mM with an optimal range of 2 to 7 mM ideally 5 mM.

The solid tissue to be digested can be washed after disaggregation with a liquid formulation containing chelating agents EGTA and EDTA to remove adhesion factors and inhibitory proteins prior to washing and removal of EDTA and EGTA prior to enzymatic digestion.

The liquid formulation required for enzymatic digestion is more optimal with minimal chelating agents EGTA and EDTA which can severely inhibit enzyme activity by removing calcium ions required for enzyme stability and activity. In addition B-mercaptoethanol, cysteine and 8-hydroxyquinoline-5-sulfonate are other known inhibitory substances.

Cryopreservation

As described in preferred embodiments final cell container for cryopreservation is a flexible container manufactured from resilient deformable material. In this embodiment of the device the final container is either transferred directly to a freezer $-20$ to $-190°$ C. or more optimally located in the controlled rate freezing apparatus either associated with the device or supplied separately (manufactured by for example Planer Products or Asymptote Ltd) in which the temperature of the freezing chamber and the flexible storage container(s) employed to contain the enriched disaggregated solid tissue container is controlled either by: injecting a cold gas (normally nitrogen for example Planer products); or by removing heat away from the controlled cooling surface(s). Both methods result in the ability to accurately control with an error of less than $1°$ C. or more preferable $0.1°$ C. the freezing process at the required rate for the specific cell(s) to be frozen based on the freezing solution and the desired viability of the product. This cryopreservation process must take into account the ice nucleation temperature which is ideally as close as possible to the melting temperature of the freezing solution. Followed by crystal growth in an aqueous solution, water is removed from the system as ice, and the concentration of the residual unfrozen solution increases. As the temperature is lowered, more ice forms, decreasing the residual non-frozen fraction which further increases in concentration. In aqueous solutions, there exists a large temperature range in which ice co-exists with a concentrated aqueous solution. Eventually through temperature reduction the solution reaches the glass transition state at which point the freezing solution and cells move from a viscous solution to a solid-like state below this temperature the cells can undergo no further biological changes and hence are stabilised, for years potentially decades, until required.

Further Applications of the Invention

The disaggregated cell products achieved by the method of the present invention can be cultured and/or analysed (characterised) according to all methods known to the person skilled in the art.

The cells obtainable by the methods disclosed herein may be used for subsequent steps such as research, diagnostics, tissue-banks, biobanks, pharmacological or clinical applications known to the person skilled in the art. Cells can then be taken into culture using a Medium optimized for this application, e.g. T cell Mixed Media (Cellular Therapeutics) usually containing but not limited to growth factors such as IL-2, IL-7, IL-15, IL-21 or stimulatory conditions such as plates or polystyrene beads coated with antibodies. In the present invention isolated cells were seeded into culture containers and maintained using procedures standardly used by a person skilled in the art such as a humidified atmosphere (1-20% usually 5% CO2, 80 to 99% usually 95% air)

at temperatures between 1 to 40 usually 37° C. for several weeks and supplements may be added supplemented with 10% FBS and 3000 IU/mL I L-2.

Such cell cultures can be used to study e.g. cell function, tumour cell killing, cell signalling, biomarkers, cell pathways, nucleic acids, and other cell or tissue related factors that may be used to identify donor, tissue, cell or nucleic acid status.

The enriched cells could be used before and/or after cell culturing as a pharmaceutical composition in the therapy, e.g. cellular therapy, or prevention of diseases. The pharmaceutical composition can be used for the treatment and/or prevention of diseases in mammals, especially humans, possibly including administration of a pharmaceutically effective amount of the pharmaceutical composition to the mammal.

The disease may be any disease, which can be treated and/or prevented through the presence of solid tissue derived cells and/or through increasing the concentration of the relevant cells in/at the relevant place, i.e. the tumours or sites of disease. The treated and/or preventively treated disease may be any disorder, e.g. cancer or a degenerative disorder. The treatment may be the transplantation of enriched, engineered or expanded cells or any combination of these and either administered to the relevant part of the body or supplied systemically.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

FURTHER SPECIFIC EXAMPLES

Example 1

Impact of the Length of Disaggregation

Figure 5A:
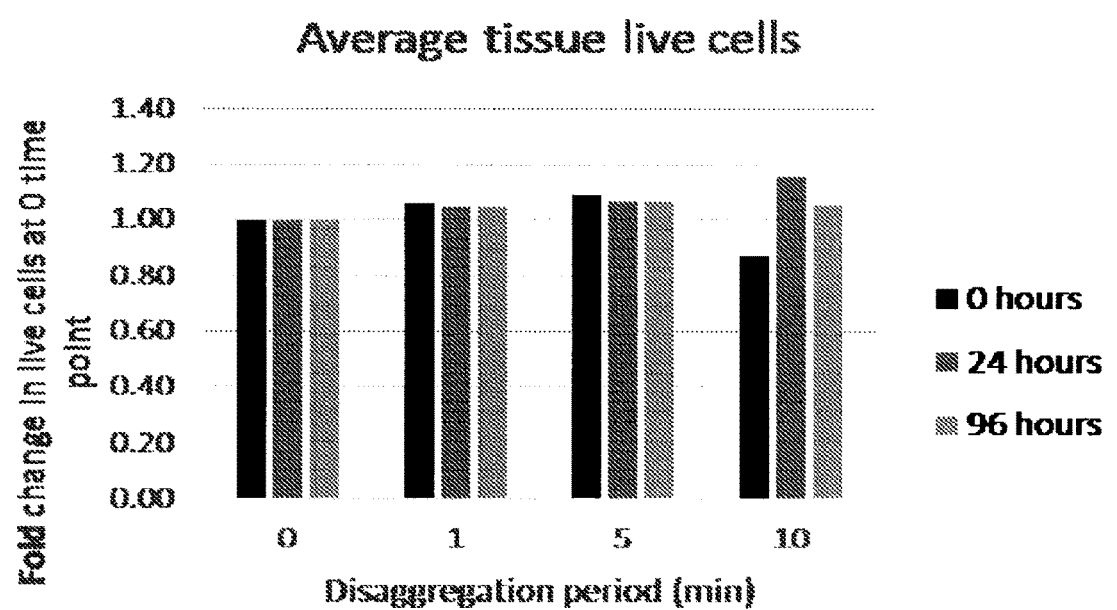
FIG. 5A (also referred to herein as FIG. 5A, and the like) depicts the average tissue live cells over time.

Peripheral blood mononuclear cells were physically disaggregated for 0, 1, 5 & 10 minutes continuously before a being cultured in vitro for 0, 24 & 96 hours to assess cell recovery. The results demonstrate the physical process has negligible impact over 1 or 5 minutes and at 10 minutes the impact was transient where and initial reduction in viable cells at 0 hours was equivalent to non-disaggregated cells at 24 & 96 hours (FIG. 5A).

Example 2

Solid tissue sample size, volume of digestion media, disaggregation and incubation times Conditions of: Solid tissue size, volume of digestion media, disaggregation time and incubation conditions have been tested and demonstrate full disaggregation of solid tissue (FIG. 5B) except where the volume of digestion media cushioned the solid tissue during the disaggregation process resulting in 30-50% of the solid tissue remaining intact.

Equivalents

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs.

The foregoing description has been presented only for the purposes of illustration and is not intended to limit the disclosure to the precise form disclosed, but by the claims appended hereto.

Non-Patent Literature Cited:

Miller R G and Phillips R A. Separation of cells by velocity sedimentation. J Cell Physiol 1969; 73: 191-201

Buckner D, Graw R G, Eisel R J, et al. Leukapheresis by continuous flow centrifugation (CFC) in patients with chronic myelocytic leukemia (CML). Blood 1969; 33: 353-369

Liu W, Hou Y, Chen H, et al. Sample preparation method for isolation of single-cell types from mouse liver for proteomic studies. Proteomics 2011; 11: 3556-3564

Nagase K, Kimura A, Shimizu T, et al. Dynamically cell separating thermo-functional biointerfaces with densely packed polymer brushes. J Mater Chem 2012; 22: 19514-19522

Rembaum A, Yen R C K, Kempner D H, et al. Cell labelling and magnetic separation by means of immunoreagents based on polyacrolein microspheres. J Immunol Methods 1982; 52: 341-351.

Cahoy J D, Emery B, Kaushal A, et al. A transcriptome database for astrocytes, neurons, and oligodendrocytes: a new resource for understanding brain development and function. J Neurosci 2008; 28:264-278

Miltenyi S, Muller W, Weichel W, et al. High gradient magnetic cell separation with MACS. Cytometry 1990; 11:231-238.

Topalian S L, Muul L M, Solomon D, et al. Expansion of human tumor infiltrating lymphocytes for use in immunotherapy trials. J Immunol Methods. 1987; 102(1):127-41.

Bonner W A, Sweet R G, Hulett H R, et al. Fluorescence activated cell sorting. Rev Sci Instrum 1972; 43: 404-409

Gossett D R, Weaver W M, Mach A J. Et al., Label-free cell separation and sorting in microfluidic systems, Anal Bioanal Chem, 2010, 397, 3249-3267

Barbara Cunha B, Peixoto C, Silva M M, et al., Filtration methodologies for the clarification and concentration of human mesenchymal stem cells, J. of Membrane Sci., 2015, 478, 117-129

Klein A B, Witonsky S G, Ahmed S A, et al. Impact of different cell isolation techniques on lymphocyte viability and function. J Immunoassay Immunochem 2006; 27: 61-76

Steinberg M S. 'ECM': its nature, origin and function in cell aggregation. Exp Cell Res 1963; 30: 257-279.

Hefeneider S H, McCoy S L, Morton J I, et al. DNA binding to mouse cells is mediated by cell-surface molecules: the role of these DNA-binding molecules as target antigens in murine lupus. Lupus 1992; 1: 167-173.

Pisetsky D S and Fairhurst A-M. The origin of extracellular DNA during the clearance of dead and dying cells—review. Autoimmunity 2007; 40: 281-284

Renner W A, Jordan M, Eppenberger H M, et al. Cell-cell adhesion and aggregation: influence on the growth behaviour of CHO cells. Biotechnol Bioeng 1993; 41: 188-193

Shedlock D J, Aviles J, Talbott K T et al., Induction of Broad Cytotoxic T Cells by Protective DNA Vaccination Against Marburg and Ebola. Molecular Therapy, 2013; 21,1432-1444

Baust J G, & Baust J M, Advances in Biopreservation, 2006, Chapt. 8, 157-196

Seglen, P. O., Preparation of Isolated Rat Liver Cells, Methods in Cell Biology, 1976; 13, 29

Quistorff, B., Dich, J., & Grunnet, N. Preparation of isolated rat liver hepatocytes. Methods in molecular biology, Chapt 14, 1990; 151-160.

Seifter, S., Gallop, P. M., Klein, L., et al. Studies on Collagen, Part II. Properties of Purified Collagenase and Its Inhibition. J. Biol. Chem. 1959; 234:285

The invention claimed is:

1. A method of aseptic tissue processing to prepare T-cells from a sample, comprising:
   obtaining T-cells from disaggregated solid tissue that has not been previously cryopreserved, wherein the disaggregated solid tissue comprises cancer cells and T-cells, and the disaggregated solid tissue is contained in a closed flexible bag containing disaggregated solid tissue comprising at least one port;
   aseptically transferring the T-cells through a port into a closed flexible bag for cell culture;
   aseptically transferring a culture medium for T-cell expansion comprising one or more growth factors selected from the group consisting of IL-2, IL-7, IL-15 and IL-21 into the closed flexible bag for cell culture through a port in the closed flexible bag for cell culture; and,
   culturing the T-cells in the closed flexible bag for cell culture to obtain a population of expanded T-cells,
   wherein the closed flexible bags are part of an aseptically closed system and the transferring and the culturing are performed without opening the closed system.

2. The method of claim 1, wherein the flexible bag containing disaggregated solid tissue further contains cell media.

3. The method of claim 1, wherein the aseptically transferring the T-cells further comprises aseptically separating the T-cells.

4. The method of claim 3, wherein the aseptically separating the T-cells is selected from the group consisting of density based separation, hydrodynamic filtration, field flow fractionation, acoustophoresis and filtration.

5. The method of claim 4, wherein the aseptically separating the T-cells is filtration.

6. The method of claim 5, wherein the filtration comprises passing the T-cells through one or more filters.

7. The method of claim 1, wherein after the culturing, storing the population of expanded T-cells.

8. The method of claim 1, wherein the population of expanded T-cells comprises engineered T-cells.

* * * * *